(12) United States Patent
Dettmar et al.

(10) Patent No.: US 6,610,667 B1
(45) Date of Patent: Aug. 26, 2003

(54) COMPOSITIONS FOR TREATMENT OF DISORDERS OF THE OESOPHAGUS

(75) Inventors: Peter William Dettmar, Patrington (GB); Paul Andrew Dickson, Walkington (GB); Frank Chadwick Hampson, Hedon (GB); Ian Gordon Jolliffe, Cottingham (GB)

(73) Assignee: Reckitt Benckiser Healthcare (UK) Limited, Slough (GB)

( * ) Notice: Subject to any disclaimer, the term of this patent is extended or adjusted under 35 U.S.C. 154(b) by 0 days.

(21) Appl. No.: 09/979,538

(22) PCT Filed: May 4, 2000

(86) PCT No.: PCT/GB00/01711

§ 371 (c)(1),
(2), (4) Date: Jan. 7, 2002

(87) PCT Pub. No.: WO00/67799

PCT Pub. Date: Nov. 16, 2000

(30) Foreign Application Priority Data

May 5, 1999 (GB) .............................................. 9910212

(51) Int. Cl.⁷ ..................... A61K 31/715; A61K 47/36; A61P 1/04
(52) U.S. Cl. ............................. 514/54; 514/4; 514/779; 514/780; 514/782; 536/124; 536/123.1; 536/114; 536/119; 536/55.1
(58) Field of Search ............................... 514/54, 4, 782, 514/779, 780; 536/55.1, 124, 123.1, 114, 119

(56) References Cited

U.S. PATENT DOCUMENTS

| 4,717,713 A | 1/1988 | Zatz et al. ..................... 514/2 |
| 5,811,123 A | * 9/1998 | Fuisz |

FOREIGN PATENT DOCUMENTS

| EP | 0 882 449 | 9/1998 |
| GB | 2 283 171 | 5/1995 |
| GB | 2 324 725 A | * 4/1998 |
| GB | 2 324 725 | 11/1998 |
| JP | 57-133170 | 8/1982 |
| WO | WO 90/14110 | 11/1990 |

* cited by examiner

*Primary Examiner*—Samuel Barts
*Assistant Examiner*—Michael C. Henry
(74) *Attorney, Agent, or Firm*—Fish & Richardson P.C.

(57) ABSTRACT

Pharmaceutical compositions having improved bioadhesive properties are produced by combining an alginate, xanthan gum and/or a carageenan gum and a glucomannan and/or a galactomannan. The composition can provide both a protecting and a healing effect on mucosal surface.

41 Claims, No Drawings

COMPOSITIONS FOR TREATMENT OF DISORDERS OF THE OESOPHAGUS

This application is a 371 of PCT/GB00/01711, filed May 4, 2000.

BACKGROUND OF THE INVENTION

The present invention relates to a compositions capable of detachable adherence to a surface. More particularly, the present invention relates to such compositions for use in coating a biological, for example, mucosal surface and/or delivering an active ingredient to the biological surface.

Many compositions are known to be bioadhesive (i.e. able to adhere to biological surfaces, e.g. mucus, the skin, mucosal surfaces, epithelium etc.) and the value of this property is well recognised. For example, bioadhesives may be used to adhere active agents to specific sites in the body for local drug administration, or to coat particular parts of the body.

However, when bioadhesives are applied to such surfaces in aqueous solution they may be easily washed off or mechanically removed because the strength of adhesion of each individual bioadhesive molecule to the surface is not very high. This may lead to further problems if the bioadhesive materials contain active agents intended for use at one particular site, but which are washed away to other sites.

This is especially true where bioadhesives are applied to the upper gastrointestinal (GI) tract where washing off by swallowed saliva and/or mucus is a particular problem.

The prior art does not provide a composition which is able to adhere to biological surfaces and which can provide both physical protection, for example, against episodes of gastric reflux as well as exert a curative effect on the surface, for example, by delivering a pharmaceutically active ingredient to the surface.

A need therefore exists for a bioadhesive pharmaceutical composition which is able to coat a biological surface to protect and heal the surface and/or to deliver an active ingredient to the surface throughout the GI tract.

The need extends to a pharmaceutical composition which is capable of detachably adhering to desired regions of the oesophagus immediately following ingestion and prior to the composition reaching the stomach, the composition being able to exhibit both a protective and a direct healing effect, whether this arises as a result of the barrier properties alone or as a consequence of the incorporation of further active ingredients in the formulation which may have a beneficial effect on the healing process, immediately after ingestion and prior to contact with the stomach.

It is also desirable that the compositions are able to resist washing off by physiological fluids such as saliva or fluids which are subsequently ingested by the user and/or refluxed from the stomach.

In addition to the above, it is important that, when in liquid form, the compositions are of such a viscosity that they are capable of being provided in and reproducibly dispensed from a single container in a form which is immediately ready for use by the consumer.

DISCLOSURE OF THE INVENTION

We have now found a novel composition for detachable adhesion on biological surfaces of mammals which satisfy some or all of the above needs. The viscosity and adhesion of the resulting formulations are such that these compositions show good adhesion, stability and wash-off resistance.

According to a first aspect of the present invention there is provided a pharmaceutical composition for the treatment of disorders of the oesophagus, the composition comprising:
   a) 0.1 to 11.0 parts by weight, preferably 2.5 to 8 parts by:weight alginate (hereinafter component a);
   b) 0.01 to 3.0 parts by weight, preferably 0.1 to 1.5 parts by weight of gum selected from xanthan gum, carageenan gum and mixtures thereof (hereinafter component b); and
   c) 0.01 to 3.0 parts by weight, preferably 0.1 to 1.5 parts by weight of gum selected from a galactomannan, a glucomannan and mixtures thereof (hereinafter component c).

The term 'alginate' is intended to encompass alginic acids, salts of alginic acids (alginate salts), derivatives of alginic acid, for example esters such as propylene glycol and mixtures thereof.

The alginate is preferably a monovalent salt of alginic acid, for example the sodium, potassium or ammonium salt, most preferably the sodium salt. Such alginates may be supplied by FMC Biopolymer AS, for example Protonal LFR5/60 and Protonal LF10L.

Preferably, the composition includes 1 to 10 parts by weight of alginate, more preferably between 2 and 9 parts by weight and most preferably between 3 and 8 parts by weight.

Preferably component b) includes a major amount of xanthan gum. Most preferably, component b) consists essentially of xanthan gum.

In the context of this specification, a major amount means that more than 50% by weight, preferably more than 70% by weight, more preferably more than 90% by weight, especially more than 95% by weight of the referenced component is present.

Component c) may be any pharmaceutically acceptable glucomannan or galactomannan, including enzymatically altered derivatives thereof. Preferably, however, component c) includes a major amount of a galactomannan. Preferably, component c) consists essentially of a galactomannan, especially locust bean gum.

Preferably components b) and c) are present in a total amount of from 0.2 to 2.5 parts by weight, more preferably 0.7 to 2 parts by weight, most preferably 1 to 1.6 parts by weight. Preferably components b) and c) are present in amount ratios of from 1:10 to 10:1, most preferably 2:8 to 8:2.

In a preferred embodiment of the present invention, b) is present in an amount greater than c) such that the ratio of b):c) is in the range 1.5:1 to 3.5:1, more preferably in the range 2:1 to 3:1, especially about 2.3:1.

It will be appreciated that the compositions according to the present invention may be presented in solid form, for example as a chewable tablet, in granular or powder form, as a gel or as a liquid. It is preferred however, that the composition is in the form of a liquid, most preferably a pourable liquid.

Pourable means flowable at room temperature (for example, 20–24° C.) (possibly following reasonably vigorous shaking) such that doses of, for example, 5 ml may be measured out with reasonable accuracy. For example, reproducible doses of as low as 5 ml may be dispensed from bottles having neck diameters of 1.5 cm or more.

Preferably the composition has a viscosity of between 500 and 10000 mPa·s, most preferably between 1000 and 8000 mPa·s measured on a Brookfield Viscometer at 20° C. using spindle No. 3.

When in the form of a liquid, it is most preferred that the compositions are aqueous liquids.

In a most preferred embodiment there is therefore provided an aqueous bioadhesive pourable liquid composition for coating a biological surface in the treatment and/or prevention of reflux oesophagitis, gastritis, dyspepsia and disorders of the oesophagus associated with reflux, the composition comprising:

a) 0.1 to 11% weight, preferably 2.5 to 8% weight alginate salt (hereinafter component a);

b) 0.01 to 3.0% weight, preferably 0.1 to 1.5% weight xanthan gum (hereinafter component b); and c) 0.01 to 3.0% weight, preferably 0.1 to 1.5% weight galactomannan or glucomannan (hereinafter component c).

Any component described herein as being included in a composition according to the invention may be included in the aqueous composition of the most preferred embodiment. Where an amount is stated in parts by weight in relation to an embodiment, the same numerical value or values expressed as "% weight" may be applied to said most preferred embodiment. Thus, by way of example, it is described above that a composition may include 1 to 10 parts by weight alginate. This may be expressed as 1 to 10% weight when applied to said most preferred formulation and so on.

Mixtures of xanthan gum and a glucomannan, or galactomannan for example locust bean gum, have been widely used as thickening and gelling agents in the food industries. However, an aqueous mixture of 1.0% weight xanthan gum and 0.4% weight locust bean gum has a viscosity of approximately 35,000 mPa·s at 20° C. measured on a Brookfield Viscometer using spindle No. 3. In effect, this has a jelly like consistency which is disadvantageous in that it is firstly difficult to reproducibly pour metered doses, for example of 5 ml, from a bottle and secondly, such a thick product does not enjoy wide consumer acceptance because of mouthfeel, appearance and the like.

The inventors have surprisingly found that the addition of certain amounts of alginate to the mixture actually reduces the viscosity of the mixture to within consumer acceptance levels.

The composition has been found to exhibit superior bioadhesive properties, particularly on mucosal tissue, such as the oesophagus.

In a preferred embodiment of the present invention, the composition is also useful in treating and/or ameliorating the effects of gastric reflux by forming a raft which floats on the stomach contents of a consumer of the product, which raft prevents reflux of the gastric contents into the oesophagus or preceding the gastric contents into the oesophagus during reflux.

It will be appreciated that the composition preceding gastric content into the oesophagus during an episode of reflux may be beneficial in that the physical barrier of the composition adhering to or coating the oesophagus because of its superior bioadhesive properties will be recharged during such an episode.

In accordance with this preferred embodiment of the present invention the composition further includes any one or more further ingredients selected from the group consisting of pharmaceutically acceptable gas forming agents, a source of di or trivalent metal ions, buffering agents, preservatives, sweeteners and flavourants.

Preferably the pharmaceutically acceptable gas forming agents are carbon dioxide ($CO_2$) forming agents, preferably alkali metal bicarbonates, for example, sodium bicarbonate, potassium bicarbonate and/or mixtures thereof. The concentration of alkali metal bicarbonate in the compositions of the invention is preferably 0.1 to 8 parts by weight, more preferably 0.5 to 5 parts by weight, even more preferably 1 to 3 parts by weight and most preferably 1.5 to 3 parts by weight.

Preferably the source of di or trivalent metal ions is suitable for cross-linking the alginate molecules in the composition to form an effective raft in the stomach. These metal ions preferably become available when the compositions reach the stomach but must not be available before then (as the compositions will gel too early). Suitable metal ions are aluminium and, preferably, calcium ions. Most preferably the compositions comprise calcium carbonate.

The compositions of the present invention therefore preferably further comprise from 0.1 to 5 parts by weight calcium carbonate, more preferably 0.5 to 3.5 parts by weight calcium carbonate, most preferably 0.75 to 3 parts by weight.

Agents for adjusting the pH, i.e. buffering agents, for example, monopotassium phosphate and/or dipotassium phosphate may be included in the composition in an amount of 0.01 to 1 parts by weight.

The compositions of the present invention may further comprise preservatives to prevent contamination and subsequent deterioration by micro-organisms. Examples of suitable preservatives are the esters of para-hydroxybenzoic acid and their salts, which are preferably used in combination. Examples of such esters include methyl, ethyl propyl and butyl para-hydroxybenzoate. Preferred concentrations for the preservatives are 0.01 to 0.5 parts by weight.

The compositions of the present invention may also include colourants, sweeteners (e.g. sodium saccharin) and/or flavourants. Preferably such ingredients are present in an amount of 0.01 to 1 parts by weight.

In the composition according to this embodiment of the present invention, the gums, for example xanthan gum and locust bean gum, act as both bioadhesive agents as well as (very valuably) the suspending agent, thereby enjoying a dual function and avoiding the need for a separate suspending agent, for example, carbomer. Preferably, therefore, the compositions according to the present invention contain no suspending agents other than the gums, for example xanthan gum and locust bean gum.

Carbomer has traditionally been used as a suspending agent in compositions including an alginate for raft formation in the stomach to prevent gastric reflux. Carbomer, in the absence of alginate, is a known bioadhesive but loses this property in the presence of alginate. Xanthan gum and locust bean gum, in contradistinction to carbomer, are suitable suspending agents whilst presenting an improved bioadhesive composition. Xanthan gum and locust bean gum are thus suited to replace carbomer as a suspending agent in compositions of this type.

The compositions of the present invention may also include further ingredients in order to enhance the desired properties of the composition. For example, additives such as simethicone may be added to increase the hydrophobicity of the formulation in order to improve its wash-off resistance.

Xanthan gum is commercially available from Kelco and Rhone Poulenc. Locust bean gum is commercially available from Carob S.A. and Rhone Poulenc.

The composition according to the invention may further include an active ingredient selected from the group consisting of acetaminophen, ibuprofen, naproxen, diclofenac, ketoprofen, choline salicylate, benzydamine, buprenorphine, hydrocortisone, betamethasone; decongestants (e.g. pseudoephedrine, phenylephrine, oxymetazoline, xylometazoline); cough suppressants (e.g. dextromethorphan, codeine, pholocodine); expectorants (e.g. guaiphenesin, n-acetylcysteine, bromhexine); antiseptics (e.g. triclosan, chloroxylenol, amylmetacresol, hexylresorcinol, dichlorobenzyl alcohol, benzyl alcohol); cardiovascular agents (e.g. glyceryl trinitrate); local anaesthetics (e.g. benzocaine, lignocaine); antacid agents (e.g. calcium carbonate, sodium bicarbonate, magnesium trisilicate, aluminium hydroxide, magaldrate,); antiulcer agents (e.g. carbenoxolone, sucralfate, cimetidine, ranitidine, nizatidine, famotidine, omeprazole, pantoprazole); antihistamines (e.g. loratidine, terfenadine, diphenhydramine, chlorphenhydramine, triprolidine, acrivastine); antinausea agents (e.g. prochlorperazine, sumatriptan); bowel regulatory agents (e.g. diphenoxylate, loperamide, sennosides); antifungal agents (e.g. clotrimazole) and antibiotics (e.g. fusafungine, tyrothricin).

Whilst the compositions according to the present invention lend themselves to either targeted delivery or sustained release of such an active ingredient, it will be appreciated that such an ingredient is preferably not included in the composition. However, where an active ingredient is included, the composition may include less than 3 parts by weight, more preferably less than 2 parts by weight, most preferably less that 1 parts by weight of the active ingredient.

The present invention represents a completely new approach to the problem of gastric reflux in that the oesophagus may be protectively coated with the composition immediately after ingestion of the composition in order to provide a physical barrier against the acid from gastric reflux. Furthermore, the coating may include ingredients which make the barrier, in effect, act as a chemical barrier (on account of the inclusion of ingredients which are able to neutralise or deactivate the acid or the pepsin which are responsible for irritation in the oesophagus) as well as a physical barrier.

It will be appreciated that the compositions according to the invention may adhere to other biological surfaces of the mammalian body, for example, the oral cavity, the back of the throat and the underside of the tongue or the stomach.

In a preferred embodiment of the present invention there is provided an aqueous bioadhesive pourable liquid composition comprising:

| | |
|---|---|
| Monopotassium phosphate | 1.00 g |
| Dipotassium phosphate | 4.00 g |
| Sodium bicarbonate | 16.8 g |
| Methyl paraben | 4.00 g |
| Propyl paraben | 0.60 g |
| Sodium saccharin | 1.00 g |
| Xanthan gum | 9.80 g |
| Calcium carbonate | 8.00 g |
| Locust bean gum | 4.20 g |
| Sodium alginate LFR5/60 | 50.00 g |
| Flavour | 0.70 g |
| Deionised water | to 1000 ml |

The compositions according to the present invention may be presented in containers-containing multiple doses for example, bottles containing from 50 to 1000 ml of a liquid product. The consumer may then dispense the correct dosage from the container for consumption.

The composition of the present invention may be provided in unit dosage form. Thus, for example, the composition may be presented in solid form as discrete tablets or capsules. Alternatively, the composition may be presented in liquid form as a chewable capsule, optionally including a plurality of compartments each containing a fill volume which together total the desired dosage.

Preferably however, the composition is presented in liquid or gel form in sachets. The sachets may vary in volume from 1 to 25 ml, preferably 5 to 20 ml.

According to a further aspect to the present invention, there is provided a method of treating and/or preventing reflux oesophagitis, gastritis, dyspepsia and/or disorders of the oesophagus associated with reflux, which method comprises administration of a pharmaceutically effective amount of a pharmaceutical composition comprising:

a) 0.1 to 11 parts by weight, preferably 2.5 to 8 parts by weight alginate, (hereinafter component a);

b) 0.01 to 3.0 parts by weight, preferably 0.1 to 1.5 parts by weight of gum selected from xanthan gum carageenan gum and mixtures thereof (hereinafter component b); and c) 0.01 to 3.0 parts by weight, preferably 0.1 to 1.5 parts by weight of gum selected from a galactomannan, a glucomannan and mixtures thereof (hereinafter component c) to a patient in need thereof.

In a preferred embodiment of this aspect to the present invention there is provided a method of treating and/or preventing reflux oesophagitis, gastritis, dyspepsia and/or disorders of the oesophagus associated with reflux, which method comprises administration of a pharmaceutically effective amount of an aqueous bioadhesive pourable liquid composition comprising:

a) 0.1 to 11% weight, preferably 2.5 to 8% weight alginate salt (hereinafter component a);

b) 0.01 to 3.0% weight, preferably 0.1 to 1.5% weight xanthan gum (hereinafter component b); and c) 0.01 to 3.0% weight, preferably 0.1 to 1.5% weight galactomannan or glucomannan hereinafter component c)

to a patient in need thereof.

According to a further aspect of the present invention there is provided a use of a composition according to the invention in the preparation of a medicament for the treatment of irritation and/or lesions in the oesophagus, diseases or irritations of the mouth, throat, pharynx and/or stomach and/or other diseases caused by or associated with reflux which treatment comprises administering a pharmaceutically effective amount of the medicament to a patient in need thereof.

According to a further aspect to the present invention there is provided the use of a composition comprising;

a) 0.1 to 11.0 parts by weight, preferably 2.5 to 8 parts by weight alginate (hereinafter component a);

b) 0.01 to 3.0 parts by weight, preferably 0.1 to 1.5 parts by weight of gum selected from xanthan gum, carageenan gum and mixtures thereof (hereinafter component b); and c) 0.01 to 3.0 parts by weight, preferably 0.1 to 1.5 parts by weight of gum selected from a galactomannan, a glucomannan and mixtures thereof (hereinafter component c)

for coating a biological surface in the treatment and/or prevention of reflux oesophagitis, gastritis, dyspepsia and/or disorders of the oesophagus associated with reflux.

In a preferred embodiment of this aspect to the present invention there is provided the use of an aqueous bioadhesive pourable liquid composition comprising:

a) 0.1 to 11% weight, preferably 2.5 to 8% weight alginate salt (hereinafter component a);
  b) 0.01 to 3.0% weight, preferably 0.1 to 1.5% weight xanthan gum (hereinafter component b); and
  c) 0.01 to 3.0% weight, preferably 0.1 to 1.5% weight galactomannan or glucomannan (hereinafter component c)

for coating a biological surface in the treatment and/or prevention of reflux oesophagitis, gastritis, dyspepsia and disorders of the oesophagus associated with reflux.

According to a further aspect to the present invention there is provided a composition comprising a) 0.1 to 11.0 parts by weight, preferably 2.5 to 8 parts by weight alginate (hereinafter component a);
  b) 0.01 to 3.0 parts by weight, preferably 0.1 to 1.5 parts by weight of gum selected from xanthan gum, carageenan gum and mixtures thereof (hereinafter component b); and
  c) 0.01 to 3.0 parts by weight, preferably 0.1 to 1.5 parts by weight of gum selected from a galactomannan, a glucomannan and mixtures thereof (hereinafter component c)

for use in a method of treatment and/or prevention of reflux oesophagitis, gastritis, dyspepsia and disorders of the oesophagus associated with reflux, which method comprises administering a pharmaceutically effective amount of the composition to a patient in need thereof.

In the preferred embodiments of the invention as described, all references to % weight are to % weight per volume.

Any feature of any aspect of any invention or embodiment described herein may be combined with any feature of any aspect of any other invention or embodiment described herein.

The invention will now be illustrated by the following examples.

EXAMPLE 1

|  | mg/10 ml |
| --- | --- |
| Monopotassium phosphate | 20.00 |
| Dipotassium phosphate | 40.00 |
| Sodium bicarbonate | 168.00 |
| Ethyl paraben | 20.00 |
| Sodium butyl paraben | 2.22 |
| Sodium saccharin | 10.00 |
| Xanthan gum | 49.00 |
| Calcium carbonate | 80.00 |
| Locust bean gum | 21.00 |
| Sodium alginate LFR5/60 | 300.00 |
| Flavour | 7.00 |
| Deionised water | to 10 ml |

Method of Manufacture

1. Add locust bean gum to the water, heat to 40° C. and mix.
2. Add sodium alginate and mix.
3. Add sodium bicarbonate, phosphates, ethyl paraben, sodium butyl paraben and sodium saccharin and mix.
3. Add xanthan gum and mix.
4. Add calcium carbonate and mix
5. Add flavour and make up to volume with water and mix.

EXAMPLE 2

| Monopotassium phosphate | 0.2% |
| --- | --- |
| Dipotassium phosphate | 0.4% |
| Sodium bicarbonate | 2.67% |
| Ethyl paraben | 0.2% |
| Sodium butyl paraben | 0.022% |
| Sodium saccharin | 0.1% |
| Xanthan gum | 0.49% |
| Calcium carbonate | 1.60% |
| Locust bean gum | 0.21% |
| Sodium alginate LFR5/60 | 5.00% |
| Flavour | 0.07% |
| Deionised water | to 100% volume |

(All percentages by weight per volume of the composition.)

Method of Manufacture Same as Example 1

EXAMPLE 3

|  | g/1000 ml |
| --- | --- |
| Monopotassium phosphate | 2.00 |
| Dipotassium phosphate | 4.00 |
| Sodium bicarbonate | 16.8 |
| Ethyl paraben | 2.00 |
| Sodium butyl paraben | 0.22 |
| Sodium saccharin | 1.00 |
| Xanthan gum | 9.80 |
| Calcium carbonate | 8.00 |
| Locust bean gum | 4.20 |
| Sodium alginate LFR5/60 | 50.00 |
| Flavour | 0.70 |
| Deionised water | to 1000 ml |

Method of Manufacture

1. Add phosphates, parabens, saccharin and sodium bicarbonate to a portion of the water and mix.
2. Add the xanthan gum and mix.
3. Add the calcium carbonate and mix.
4. Add the locust bean gum and mix.
5. Add the sodium alginate and mix.
6. Add the flavour, make up to volume and mix.

EXAMPLE 4

|  | mg/10 ml |
| --- | --- |
| Monopotassium phosphate | 20.00 |
| Dipotassium phosphate | 40.00 |
| Sodium bicarbonate | 168.00 |
| Ethyl paraben | 20.00 |
| Sodium butyl paraben | 2.20 |
| Sodium saccharin | 10.00 |
| Xanthan gum | 49.00 |
| Calcium carbonate | 80.00 |
| Locust bean gum | 21.00 |
| Simethicone | 100.00 |
| Sodium alginate LFR5/60 | 100.00 |
| Sodium alginate LF10L | 100.00 |
| Flavour | 0.70 |
| Deionised water | to 10 ml |

Method of Manufacture

1. Add phosphates to the water and mix
2. Add sodium bicarbonate, ethyl paraben, sodium butylparaben and sodium saccharin to (1) and mix.

3. Add xanthan gum to (2) and mix.
4. Add calcium carbonate to (3) and mix
5. Add locust bean gum to (4) and mix.
6. Add simethicone to (5) and mix
7. Dry blend the two sodium alginates and add to (6) and mix
8. Add flavour and make up to volume with water and mix.

EXAMPLE 5

|  | mg/10 ml |
| --- | --- |
| Monopotassium phosphate | 20.00 |
| Dipotassium phosphate | 40.00 |
| Sodium bicarbonate | 168.00 |
| Ethyl paraben | 20.00 |
| Sodium butyl paraben | 2.22 |
| Sodium saccharin | 10.00 |
| Xanthan gum | 49.00 |
| Calcium carbonate | 80.00 |
| Locust bean gum | 21.00 |
| Sodium alginate LF10L | 250.00 |
| Flavour | 7.00 |
| Deionised water | to 10 ml |

Method of Manufacture Same as Example 3

EXAMPLE 6

|  |  |
| --- | --- |
| Monopotassium phosphate | 1.00 g |
| Dipotassium phosphate | 4.00 g |
| Sodium bicarbonate | 16.8 g |
| Methyl paraben | 4.00 g |
| Propyl paraben | 0.60 g |
| Sodium saccharin | 1.00 g |
| Xanthan gum | 9.80 g |
| Calcium carbonate | 8.00 g |
| Locust bean gum | 4.20 g |
| Sodium alginate LFR5/60 | 50.00 g |
| Flavour | 0.70 g |
| Deionised water | to 1000 ml |

Method of Manufacture

1. Add the locust bean gum to a portion of the water and heat to 40° C.
2. To a separate portion of the water add sodium alginate, the phosphates, sodium bicarbonate, parabens and saccharin and mix.
3. To a third portion of the water add xanthan gum and mix.
4. Add (2) to (1) and mix.
5. Add (3) to (4) and mix.
6. Add calcium carbonate, flavour, make up to volume and mix.

EXAMPLE 7

A comparative study of the composition according to a preferred embodiment of the invention with a known liquid gastrointestinal product (Gaviscon Liquid (Registered Trade Mark)) is undertaken. The adhesion of the compositions to an artificial surface is determined as an indicator of oesophageal bioadhesion. The products are applied to a length of visking tubing set at an angle to the horizontal in a humid environment. The products are eluted from the tubing with a constant flow of water and the amount of product remaining on the tubing is monitored by weight.

At least three replicate experiments are performed with each product and the recorded timings averaged.

The results of the comparative study are set out below.

TABLE 3

Comparative Study of Oesophageal Bioadhesion by Example 3, Example 5 and Gaviscon Liquid (RTM)

| Time (minutes) | % Adhesion | | |
| --- | --- | --- | --- |
|  | Example 3 | Example 5 | Gaviscon Liquid (RTM) |
| 2.00 | 17.00 | 40.00 | 10.00 |
| 4.00 | 9.00 | 15.00 | 3.00 |
| 6.00 | 8.00 | 11.00 | 1.00 |
| 8.00 | 7.00 | 10.00 | 0.00 |
| 10.00 | 7.00 | 9.00 | 0.00 |
| 12.00 | 6.00 | 10.00 | 0.00 |
| 14.00 | 4.00 | 10.00 | 0.00 |
| 16.00 | 5.00 | 7.00 | 0.00 |
| 18.00 | 4.00 | 7.00 | 0.00 |
| 20.00 | 4.00 | 3.00 | 0.00 |
| 22.00 | 4.00 | 3.00 | 0.00 |
| 24.00 | 3.00 | 1.00 | 0.00 |
| 26.00 | 3.00 | 0.00 | 0.00 |
| 28.00 | 0.00 | 0.00 | 0.00 |

EXAMPLE 8

|  |  | per tablet: |
| --- | --- | --- |
| 1. | Alginate H120L | 250 mg |
| 2. | Xanthan gum | 35 mg |
| 3. | Locust bean gum | 15 mg |
| 4. | Xylitol | 300 mg |
| 5. | Mannitol | 1225 mg |
| 6. | Povidone K30 | 100 mg |
| 7. | Flavour | 25 mg |
| 8. | Magnesium stearate | 50 mg |

Method of Manufacture

1. Dry blend 1, 2, 3, 4 and 5.
2. Granulate using a solution of 6 in isopropanol, dry at 50° C.
3. Pass the dried granules through a 1000 micron mesh.
4. Add 7 and 8 to the granules, mix for 3 minutes and press-into tablets.

EXAMPLE 9

The formulation of Example 3 is packed into foil lined sachets each containing 10 millilitres of the composition. The contents of the sachets may be dispensed by tearing off a portion of the sachet and extruding the contents of the sachet into the mouth.

EXAMPLE 10

Different aqueous mixtures of 1.0% weight/volume xanthan gum and 0.4% weight/volume locust bean gum including different sodium alginate contents were made up and their viscosities measured. The results are set out below.

TABLE 1

Viscosity v Sodium Alginate % weight for a 1.0%
weight Xanthan Gum and 0.4% weight Locust Bean Gum

| Sodium Alginate (% weight/volume) | Viscosity (measured on a Brookfield Viscometer at 20° C. using spindle 3.) (mpa · s) |
| --- | --- |
| 0.00 | 34760.00 |
| 2.50 | 6930.00 |
| 5.00 | 1135.00 |
| 7.50 | 2588.00 |
| 10.00 | 5750.00 |
| 12.50 | 28280.00 |
| 15.00 | 37000.00 |

As can be seen from Table 1 above, sodium alginate concentrations of between 2.5% weight and 10% weight reduce the viscosity of a 1.0% weight xanthan gum and 0.4% weight locust bean gum mixture to below 7000 mPa·s. Such a product is then pourable and enjoys consumer acceptance.

EXAMPLE 11

Using a constant sodium alginate concentration of 5% weight/volume and varying the total xanthan gum and locust bean gum concentration, the following table is obtained.

TABLE 2

Viscosity v Total % weight Xanthan Gum and Locust Bean Gum

| Total Content Xanthan Gum and Locust Bean Gum (% weight/volume) | Viscosity (measured on a Brookfield Viscometer at 20° C. using spindle 3.) (mpa · s) |
| --- | --- |
| 0.7 | 576 |
| 1.0 | 948 |
| 1.4 | 1,135 |
| 2.0 | 2,108 |

Table 2 clearly illustrates that particularly acceptable viscosities are achieved with total gum content below 2% weight.

What is claimed is:

1. A method of treating or preventing irritations and/or lesions in the oesophagus caused by or associated with gastric reflux, for treating or preventing diseases and/or irritations of the mouth, throat, pharynx or stomach caused by or associated with gastric reflux, and for treating and/or preventing other diseases caused by or associated with gastric reflux, which method comprises administering to a patient in need of treatment a pharmaceutically effective amount of a composition comprising (a) from 0.1 to 11.0 parts by weight of a monovalent alginate salt,
   (b) from 0.1 to 3.0 parts by weight of a gum selected from xanthan gum, carageenan gum and mixtures thereof, and
   (c) from 0.1 to 3.0 parts by weight of gum selected from a galactomannan, a glucomannan and mixtures thereof.

2. A method according to claim 1 in which component (a) is present in the amount of 2.5 to 8 parts by weight, component (b) is present in the amount of from 0.1 to 1.5 parts by weight, and component (c) is present in an amount of from 0.1 to 1.5 parts by weight.

3. A method according to claim 1 wherein the alginate is a sodium, potassium or ammonium salt.

4. A method according to claim 3 in which the alginate is sodium alginate.

5. A method according to claim 3 in which the composition has a viscosity of between 500 and 10,000 mPa·s measured on a Brookfield Viscometer at 20° C. using spindle No. 3.

6. A method according to claim 3 in which components (b) and (c) are present in the composition in total amount of from 0.2 to 2.5 parts by weight.

7. A method according to claim 6 in which components (b) and (c) are present in the composition in total amount of from 0.7 to 2 parts by weight.

8. A method according to claim 7 in which components (b) and (c) are present in the composition in total amount of between 1.0 and 1.6 parts by weight.

9. A method according to claim 3 in which components (b) and (c) are present in the composition in amount ratios of from 1:10 to 10:1.

10. A method according to claim 9 in which components (b) and (c) are present in the composition in amount ratios of from 2:8 to 8:2.

11. A method according to claim 3 in which component (c) consist essentially of a galactomannan.

12. A method according to claim 3 in which component (c) consist essentially of locust bean gum.

13. A method according to claim 3 in which the composition additionally contains a source of carbon dioxide.

14. A method according to claim 13 in which the source of carbon dioxide is sodium bicarbonate and/or potassium bicarbonate.

15. A method according to claim 13 which the composition additionally contains a source of di- or tri-valent cations.

16. A method according to claim 13 in which the composition additionally contains calcium ions.

17. A method according to claim 3 in which the composition additional contains an active ingredient selected from the group consisting of: acetaminophen; ibuprofen; naproxen; diclofenac; ketoprofen; choline salicylate; benzydamine; buprenorphine; hydrocortisone; betamethasone; decongestants such as pseudoephedrine, phenylephrine, oxymetazoline and xylometazoline; cough suppressants such as dextromethorphan, codeine and pholocodine; expectorants such as guaiphenesin, N-acetylcysteine, and bromhexine; antiseptics such as triclosan, chloroxylenol, amylmetacresol, hexylresorcinols, dichlorobenzyl alcohol and benzyl alcohol; cardiovascular agents such as glyceryl trinitrate; local anaesthetics such as benzocaine and lignocaine; antacid agents such as calcium carbonate, sodium bicarbonate, magnesium trisilicate, aluminium hydroxide and magaldrate; antiulcer agents such as carbenoxolone, sucralfate, cimetidine, ranitidine, nizatidine, famotidine, omeprazole and pantoprazole; antihistamines such as loratidine, terfenadine, diphenhydramine, chlorphenhydramine, triprolidine and acrivastine; antinausea agents such as prochlorperazine and sumatriptan; bowel regulatory agents such as diphenoxylate, loperamide, and sennosides; antifungal agents such as clotrimazole; antibiotics such as fusafungine and tyrothricine; and pharmaceutically acceptable mixtures thereof.

18. A method according to claim 3 in which the composition comprises

| | |
|---|---|
| monopotassium phosphate | 1.00 g |
| dipotassium phosphate | 4.00 g |
| sodium bicarbonate | 16.8 g |
| methyl parben | 4.00 g |
| propyl paraben | 0.60 g |
| sodium saccharin | 1.00 g |
| xanthan gum | 9.80 g |
| calcium carbonate | 8.00 g |
| locust bean gum | 4.20 g |
| sodium alginate LFR5/60 | 50.00 g |
| flavour | 0.70 g |
| deionised water | to 1000 ml |

19. A method according to claim 3 in which the composition is presented in unit dosage form.

20. A method according to claim 3 in which the composition is presented in a sachet.

21. A method for treating or preventing reflux oesophagitis, gastritis, dyspepsia and disorders of the oesophagus associated with gastric reflux, which method comprises administering to a patient in need of treatment a pharmaceutically effective amount of a composition comprising (a) from 0.1 to 11.0 parts by weight of an alginate, (b) from 0.01 to 3.0 parts by weight of a gum selected from xanthan gum, carageenan gum and mixtures thereof, and (c) from 0.01 to 3.0 parts by weight of a gum selected from a galactomannan, a glucomannan and mixtures thereof.

22. A method according to claim 21 in which component (a) is present in an amount of from 2.5 to 8 parts by weight, component (b) is present in an amount of from 0.1 to 1.5 parts by weight and component (c) is present in the amount of from 0.1 to 1.5 parts by weight.

23. A method according to claim 21 in which the alginate is sodium alginate.

24. A method according to claim 21 in which the composition has a viscosity of between 500 and 10,000 mPa·s measured on a Brookfield Viscometer at 20° C. using spindle No. 3.

25. A method according to claim 23 in which components (b) and (c) are present in the composition in a total amount of from 0.7 to 2 parts by weight.

26. A method according to claim 25 in which components (b) and (c) are present in the composition in amount ratios of from 2:8 to 8:2.

27. A method according to claim 23 in which component (c) consists essentially of locust bean gum.

28. A method according to claim 21 in which the composition additionally contains sodium bicarbonate and/or potassium bicarbonate.

29. A method according to claim 28 in which the composition additionally contains calcium ions.

30. A method according to claim 21 in which the composition comprises

| | |
|---|---|
| monopotassium phosphate | 1.00 g |
| dipotassium phosphate | 4.00 g |
| sodium bicarbonate | 16.8 g |
| methyl paraben | 4.00 g |
| propyl paraben | 0.60 g |
| sodium saccharin | 1.00 g |
| xanthan gum | 9.80 g |
| calcium carbonate | 8.00 g |
| locust bean gum | 4.20 g |
| sodium alginate LFR5/60 | 50.00 g |
| flavour | 0.70 g |
| deionised water | to 1000 ml |

31. A pharmaceutical composition for the treatment of disorders of the oesophagus, which comprises (a) from 0.1 to 11.0 parts by weight of an alginate, (b) from 0.01 to 3.0 parts by weight of a gum selected from xanthan gum, carageenan gum and mixtures thereof, and (c) from 0.01 to 3.0 parts by weight of a gum selected from a galactomannan, a glucomannan and mixtures thereof.

32. A composition according to claim 31 in which component (a) is present in an amount of from 2.5 to 8 parts by weight, component (b) is present in an amount of from 0.1 to 1.5 parts by weight and component (c) is present in the amount of from 0.1 to 1.5 parts by weight.

33. A composition according to claim 31 in which the alginate is sodium alginate.

34. A composition according to claim 31 which has a viscosity of between 500 and 10,000 mPa·s measured on a Brookfield Viscometer at 20° C. using spindle No. 3.

35. A composition according to claim 33 in which components (b) and (c) are present in a total amount of from 0.7 to 2 parts by weight.

36. A composition according to claim 35 in which components (b) and (c) are present in amount ratios of from 2:8 to 8:2.

37. A composition according to claim 33 in which component (c) consists essentially of locust bean gum.

38. A composition according to claim 31 which additionally contains sodium bicarbonate and/or potassium bicarbonate.

39. A composition according to claim 38 which additionally contains calcium ions.

40. A composition according to claim 31 which the composition comprises

| | |
|---|---|
| monopotassium phosphate | 1.00 g |
| dipotassium phosphate | 4.00 g |
| sodium bicarbonate | 16.8 g |
| methyl paraben | 4.00 g |
| propyl paraben | 0.60 g |
| sodium saccharin | 1.00 g |
| xanthan gum | 9.80 g |
| calcium carbonate | 8.00 g |
| locust bean gum | 4.20 g |
| sodium alginate LFR5/60 | 50.00 g |
| flavour | 0.70 g |
| deionised water | to 1000 ml |

41. A composition according to claim 31 presented in unit dosage form.

* * * * *